US006992109B1

(12) United States Patent
Segal et al.

(10) Patent No.: US 6,992,109 B1
(45) Date of Patent: Jan. 31, 2006

(54) METHOD FOR THE TREATMENT OF INCONTINENCE

(76) Inventors: Catherine A. Segal, 15 Dogwood Dr., Chester, NJ (US) 07930; Leslie Magnus, 52 Westmount Dr., Livingston, NJ (US) 07039

( * ) Notice: Subject to any disclaimer, the term of this patent is extended or adjusted under 35 U.S.C. 154(b) by 0 days.

(21) Appl. No.: 09/958,387

(22) PCT Filed: Jan. 27, 2000

(86) PCT No.: PCT/US00/02141

§ 371 (c)(1),
(2), (4) Date: Mar. 5, 2002

(87) PCT Pub. No.: WO00/61135

PCT Pub. Date: Oct. 19, 2000

Related U.S. Application Data

(60) Provisional application No. 60/128,347, filed on Apr. 8, 1999.

(51) Int. Cl.
*A61K 31/195* (2006.01)
(52) U.S. Cl. .................. 514/561; 514/567; 514/568
(58) Field of Classification Search ............... 514/264, 514/561, 567, 570, 568
See application file for complete search history.

(56) References Cited

U.S. PATENT DOCUMENTS

| 5,025,035 | A | * | 6/1991 | Wallace ...................... 514/530 |
| 5,189,026 | A | * | 2/1993 | Costa et al. .................. 514/30 |
| 6,001,876 | A | * | 12/1999 | Singh ......................... 514/561 |
| 6,028,214 | A | * | 2/2000 | Silverman et al. .......... 560/188 |
| 6,127,418 | A | * | 10/2000 | Bueno et al. ................ 514/561 |
| 6,242,488 | B1 | * | 6/2001 | Bueno et al. ................ 514/561 |
| 6,306,910 | B1 | * | 10/2001 | Magnus et al. ............. 514/561 |
| 6,326,374 | B1 | * | 12/2001 | Magnus et al. ......... 514/263.31 |
| 6,544,998 | B2 | * | 4/2003 | Mylari ....................... 514/256 |

FOREIGN PATENT DOCUMENTS

| WO | 9209560 | | 6/1992 |
| WO | WO 93/23383 | * | 11/1993 |
| WO | WO 97/33858 | * | 9/1997 |
| WO | 9809948 | | 3/1998 |
| WO | 0012692 | | 3/2000 |

OTHER PUBLICATIONS

Gil-Nagel et al., "Incontinence during treatment with gabapentin", *Neurology*, vol. 48, No. 5, 1997, pp 1467-1468.
Doherty et al., "Gabapentin in a medically refractory epilepsy population: seizure response and unusual side effects", *Epilepsia*, vol. 36, No. 4, 1995, p 71.
Igawa et al., "Effects of GABA-receptor stimulation and blockade on micturition in normal rats and rats with bladder outflow obstruction", *The Journal of Urology*, vol. 150, 1993, pp. 537-542.
Maggi et al., "Neuroeffector mechanisms in the voiding cycle of the guinea pig urinary bladder", *J. Auton. Pharmacol.*, vol. 7, 1987, pp 295-308.
Taylor, M.C., et al., British Journal of Urology. 51 pp. 504-505 (1979).
The Physicians' Desk Reference. 52, pp. 2110-2113 (1998).

* cited by examiner

*Primary Examiner*—Christopher S. F. Low
*Assistant Examiner*—Brian-Yong S. Kwon
(74) *Attorney, Agent, or Firm*—Gregg C. Benson; Carl J. Goddard

(57) ABSTRACT

The instant invention is a method of using certain analogs of glutamic acid and gamma-aminobutyric acid to treat incontinence.

8 Claims, No Drawings

METHOD FOR THE TREATMENT OF INCONTINENCE

This application is a 371 of PCT/US00/02141 Jan. 27, 2000 which claims benefit of 60/128,347 Apr. 8, 1999.

BACKGROUND OF THE INVENTION

1. Field of the Invention

The present invention relates to the use of analogs of glutamic acid and gamma-aminobutyric acid (GABA) for the treatment of incontinence.

2. Description of Related Art

GABA analogs are known agents useful in antiseizure therapy for central nervous system disorders such as epilepsy, Huntington's chorea, cerebral ischemia, Parkinson's disease, tardive dyskinesia, and spasticity, It has also been suggested that the compounds can be used as antidepressants, anxiolytics, and antipsychotics. See WO 92/09560 (U.S. Ser. No. 618,692 filed Nov. 27, 1990) and WO 93/23383 (U.S. Ser. No. 886,080 filed May 20, 1992).

WO 97/33858 teaches that compounds related to gabapentin are useful or treating epilespy, faintness attacks, hypokinesia, cranial disorders, neurodegenerative disorders, depression, anxiety, panic, pain, and neuropathological disorders. WO 97/33858 does not specify what forms of pain are treated.

Additionally, the compounds of the invention are known for treatment of neuropathic pain. For example, see Rosner H; Rubin L; Kestenbaum A., Gabapentin adjunctive therapy in neuropathic pain states. Clin J Pain, 1996 Mar, 12:1, 56–8; Segal A Z; Rordorf G., Gabapentin as a novel treatment for postherpetic neuralgia. Neurology, 1996 Apr, 46:4, 1175–6; Wetzel C H; Connelly J F., Use of gabapentin in pain management. Ann Pharmacother, 1997 September, 31:9, 1082–3; Zapp J J., Postpoliomyelitis pain treated with gabapentin [letter]. Am Fam Physician, 1996 Jun, 53:8, 2442, 2445; Cheville A, et al., Neuropathic pain in radiation myelopathy: a case report. Program book, American Pain Society (14th Annual Scientific Meeting). Abstract #95823, p. A-115; Sist T; Filadora V; Miner M; Lema M., Gabapentin for idiopathic trigeminal neuralgia: report of two cases. Neurology, 1997 May, 48:5, 1467; Waldman S D, Tutorial 28: Evaluation and Treatment of Trigeminal Neuralgia. Pain Digest (1997) 7:21–24; Mellick LB; Mellick G A., Successful treatment of reflex sympathetic dystrophy with gabapentin [letter]. Am J Emerg Med, 1995 Jan, 13:1, 96; Mellick G A; Seng M I., The use of gabapentin in the treatment of reflex sympathetic dystrophy and a phobic disorder. Am J Pain Manage 1995; 5:7–9; Mellick G A; Mellicy L B; Mellick L B., Gabapentin in the management of reflex sympathetic dystrophy [letter]. J Pain Symptom Manage, 1995 May, 10:4, 265–6; Mellick G A; Mellick L B., Reflex sympathetic dystrophy treated with gabapentin. Arch Phys Med Rehabil, 1997 Jan, 78:1, 98–105 and Mackin G A., Medical and pharmacologic management of upper extremity neuropathic pain syndromes. J Hand Ther, 1997 Apr–Jun, 10:2, 96–109.

Urinary incontinence (UI) is often described as either urge incontinence, where urine lost is associated with a sudden or strong desire to void, or stress incontinence, where urine loss is associated with coughing, laughing, or physical exercise. A more general category, mixed incontinence, includes those patients showing both stress and urge symptoms.

Although urinary incontinence is quite prevalent, it is still under-diagnosed and under-reported. The U.S. Department of Health and Human Services estimates that UI affects over 13 million Americans at a cost in excess of #15 billion per year. Many victims of UI do not seek help because of embarrassment or a perception that nothing can be done about their problem. Consequently, the general health and social life of these victims may be significantly compromised for years.

SUMMARY OF THE INVENTION

The invention related to methods for treating patients having urinary incontinence. In methods according to the invention, compositions comprising a gaba analog in a pharmaceutically-acceptable vehicle are administered to a patient suffering from urinary incontinence.

This invention provides a method for treating incontinence in a mammal comprising administering to a subject suffering from incontinence an effective amount of a GABA analog. A preferred embodiment utilizes a cyclic amino acid compound of Formula I

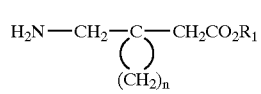

wherein $R_1$ is hydrogen or lower alkyl selected from the group consisting of a straight or branched chain alkyl of from 1 to 8 carbon atoms and n is an integer of from 4 to 6, and the pharmaceutically acceptable salts thereof. An especially preferred embodiment utilizes a compound of Formula I where $R_1$ is hydrogen and n is 4, which compound is I-(aminomethyl)-cyclohexane acetic acid, known generically as gabapentin.

In another embodiment, the invention includes treating incontinence with a compound of Formula II.

Formula II

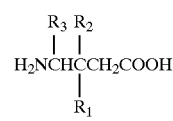

or a pharmaceutically acceptable salt thereof wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl.

Preferred compounds of the invention are those wherein $R_3$ and $R_2$ are hydrogen, and $R_1$ is $-(CH_2)_{0-2}$-i $C_4H_9$ as an (R), (S), or (R,S) isomer.

The more preferred compounds of Formula II invention are (S)-3-(aminomethyl)-5-methyl-hexanoic acid and 3-aminomethyl-5-methyl-hexanoic acid, now known generically as pregabalin.

DETAILED DESCRIPTION OF THE PREFERRED EMBODIMENTS

The method of this invention utilizes any GABA analog. A GABA analog is any compound derived from or based upon gamma-aminobutyric acid. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175, which is incorporated herein by reference. Another preferred method utilizes the GABA analogs of Formula II, and these are described in U.S. Pat. No. 5,563,175 which is incorporated herein by reference.

All that is required to practice the method of this invention is to administer a GABA analog in an amount that is effective to treat incontinence. Such amounts will generally be from about 1 to about 300 mg per kg of subject body weight. Typical doses will be from about 10 to about 5000 mg per day for an adult subject of normal weight. It is expected that common doses that might be administered could be from 100 mg three times a day up to 600 mg four times a day. Commercially available capsules of 100 mg, 300 mg, and 400 mg of gabapentin can be administered. Alternate forms include liquids and film-coated tablets.

If a compound of Formula II, such as pregabalin is used, the dosage level is one sixth that of gabapentin. The dosage range for pregabalin is from about 0.15 mg to about 50 mg per kg per day of subject body weight. Typical dosages for pregabalin will be from about 1.6 mg to about 840 mg per day with individual dosages ranging from abut 0.15 mg to about 65 mg per dose.

While not wishing to be bound by any theory, the inventors believe that the gaba analogs work to control incontinence in the following manner. Incontinence is not associated with pain. A person can sense a full bladder. In overflow incontinence, such as which occurs after a stroke, the feedback loop from the bladder to the brain is broken and the bladder fills and fills until it overflows. This mechanism would be different for urge and stress incontinence. Applicants believe that over sensitivity and irritability of the nerve endings on the bladder sphincter escalate to the point of urge incontinence. Therefore a product that stabilizes and reduces the sensitivity of these nerve fibers breaks the cycle that leads to failure of the muscular control of the sphincter.

The compounds used in the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of the Formula II can contain one or several asymmetric carbon atoms. The invention includes the individual diastereomers or enantiomers, and the mixtures thereof. The individual diastereomers or enantiomers may be prepared or isolated by methods already well-known in the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses.

Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 20 and 800 mg. The dosage is within the dosing range used in treatment of pain or as would be with the needs of the patient as described by the physician.

While the invention has been described in detail and with reference to specific examples thereof, it will be apparent to one skilled in the art that various changes and modifications can be made therein without departing from the spirit and scope thereof.

What is claimed is:

1. A method for treating a mammal suffering from urinary incontinence comprising administering to said mammal a pharmaceutical composition comprising a GABA analog in an amount sufficient to alleviate symptoms of urinary incontinence, wherein the GABA analog is the compound according to Formula I:

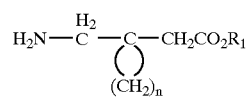

wherein $R_1$ is hydrogen or lower alkyl selected from the group consisting of a straight or branched chain alkyl of from 1 to 8 carbon atoms and n is an integer of from 4 to 6, and the pharmaceutically acceptable salts thereof.

2. The method according to claim 1, wherein Formula I comprises gabapentin.

3. The method according to claim 1, comprising from about 10 mg to about 400 mg of Formula I.

4. The method according to claim 2, comprising from about 10 mg to about 400 mg of gabapentin.

5. A method for treating a mammal suffering from urinary incontinence comprising administering to said mammal a pharmaceutical composition comprising a GABA analog in an amount sufficient to alleviate symptoms of urinary incontinence, wherein the GABA analog is the compound according to Formula II:

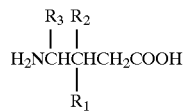

II or a pharmaceutically acceptable salt thereof wherein $R_1$ is a straight or branched chain alkyl of from 1 to 6 carbon atoms, phenyl, or cycloalkyl of from 3 to 6 carbon atoms;

$R_2$ is hydrogen or methyl; and $R_3$ is hydrogen, methyl, or carboxy.

6. The method according to claim 5, wherein the Formula II comprises pregabalin.

7. The method according to claim 5, comprising from about 0.15 to about 65 mg of Formula II.

8. The method according to claim 6, comprising from about 0.15 to about 65 mg of pregabalin.

* * * * *